(12) United States Patent
Kono

(10) Patent No.: US 12,103,255 B2
(45) Date of Patent: Oct. 1, 2024

(54) WAFER LENS ARRAY, LAYERED LENS ARRAY, IMAGE PICKUP UNIT, METHOD FOR MANUFACTURING LAYERED LENS ARRAY, AND ENDOSCOPE

(71) Applicant: OLYMPUS CORPORATION, Tokyo (JP)

(72) Inventor: Kentaro Kono, Fukushima (JP)

(73) Assignee: OLYMPUS CORPORATION, Tokyo (JP)

(*) Notice: Subject to any disclaimer, the term of this patent is extended or adjusted under 35 U.S.C. 154(b) by 731 days.

(21) Appl. No.: 17/119,114

(22) Filed: Dec. 11, 2020

(65) Prior Publication Data

US 2021/0093176 A1 Apr. 1, 2021

Related U.S. Application Data

(63) Continuation of application No. PCT/JP2018/029608, filed on Aug. 7, 2018.

(51) Int. Cl.
| | |
|---|---|
| *H01L 27/14* | (2006.01) |
| *A61B 1/04* | (2006.01) |
| *A61B 1/05* | (2006.01) |
| *A61B 1/055* | (2006.01) |
| *B29D 11/00* | (2006.01) |
| *G02B 13/00* | (2006.01) |
| *H01L 27/146* | (2006.01) |

(52) U.S. Cl.
CPC ......... *B29D 11/00307* (2013.01); *A61B 1/04* (2013.01); *A61B 1/051* (2013.01); *A61B 1/055* (2013.01); *B29D 11/00298* (2013.01); *G02B 13/0085* (2013.01); *H01L 27/14627* (2013.01)

(58) Field of Classification Search
CPC ........ B29D 11/00307; B29D 11/00298; A61B 1/04; A61B 1/051; A61B 1/055; G02B 13/0085; H01L 27/14627
USPC .......................................................... 257/294
See application file for complete search history.

(56) References Cited

U.S. PATENT DOCUMENTS 9,526,402 B2* 12/2016 Honda ............... A61B 1/00091
2004/0047274 A1 3/2004 Amanai
(Continued)

FOREIGN PATENT DOCUMENTS

| | | |
|---|---|---|
| JP | 2004-088713 A | 3/2004 |
| JP | 2010-091986 A | 4/2010 |
| JP | 2018-050769 A | 4/2018 |

OTHER PUBLICATIONS

International Search Report dated Sep. 18, 2018 received in PCT/JP2018/029608.

*Primary Examiner* — Ori Nadav
(74) *Attorney, Agent, or Firm* — Scully, Scott, Murphy & Presser, P.C.

(57) ABSTRACT

A wafer lens array includes a wafer lens formed by arranging a plurality of plate members on a plane, each plate member including a first window configured to allow light for forming an optical image to pass through, a first light-shielding portion formed on an outer circumference of the first window and a second window formed on an outer circumferential side of the first light-shielding portion and configured to allow illumination light to pass through, and the wafer lens in plurality are coaxially layered and the layered wafer lenses are bonded and fixed together in a region of the second window.

17 Claims, 11 Drawing Sheets

(56) References Cited

U.S. PATENT DOCUMENTS

2005/0089286 A1\* 4/2005 Hatori .................... A61B 1/012
385/117
2013/0165752 A1 6/2013 Chou
2016/0353983 A1\* 12/2016 Onoe ................... G02B 23/243

\* cited by examiner

WAFER LENS ARRAY, LAYERED LENS ARRAY, IMAGE PICKUP UNIT, METHOD FOR MANUFACTURING LAYERED LENS ARRAY, AND ENDOSCOPE

CROSS REFERENCE TO RELATED APPLICATION

This application is a continuation application of PCT/JP2018/029608 filed on Aug. 7, 2018, the entire contents of which are incorporated herein by this reference.

BACKGROUND OF THE INVENTION

1. Field of the Invention

The present invention relates to a wafer lens array obtained by coaxially layering, and bonding and fixing a plurality of wafer lenses, each of which is formed by arranging a plurality of optical elements on a plane, a layered lens array formed by cutting out the wafer lens array for each predetermined region, an image pickup unit including the layered lens array and an image pickup device on which an optical image is formed, a method for manufacturing the layered lens array, and an endoscope using the layered lens array as an image pickup optical system and an illumination optical system.

2. Description of the Related Art

Conventionally, endoscopes with an elongated tube-shaped insertion portion have been widely used, for example, in medical and industrial fields. Among such endoscopes, medical endoscopes used in the medical field are configured to be able to observe organs with an insertion portion inserted into, for example, a body cavity of a living body or perform various kinds of treatment, if necessary, using a treatment instrument inserted into a treatment instrument insertion channel provided for the endoscope for the organs or the like. On the other hand, industrial endoscopes used in the industrial field are configured to be able to observe and inspect a state of damage, corrosion or the like inside an apparatus or machinery such as a jet engine or factory piping with the insertion portion inserted into the apparatus or machinery.

Such endoscopes, medical endoscopes used in the medical field in particular, are always required to reduce a diameter of a distal end portion of an insertion portion or reduce and shorten a rigid length of a distal end rigid member to improve insertability when the insertion portion is inserted into the body cavity of a living body.

Various component units (e.g., an image pickup unit including an image pickup optical system, an image pickup device and an image pickup substrate or the like, a treatment instrument insertion channel, a light guide fiber bundle for illumination) are generally disposed inside the distal end rigid member provided at the distal end portion of the insertion portion of such an endoscope.

Therefore, in order to reduce a diameter of the distal end portion of the insertion portion or reduce the size and shorten the rigid length of the distal end rigid member, for example, arrangement of various component units provided inside the distal end rigid member is being contrived or efforts are being made to reduce the sizes of the respective component units.

For example, in recent years, a layered lens array has been proposed as a contrivance for miniaturization of an image pickup optical system and an illumination optical system constituting part of the image pickup unit, the layered lens array being formed by coaxially layering, and bonding and fixing a plurality of optical elements (optical lenses made of glass or resin molded product) in an optical axis direction, and a variety of endoscopes using such a layered lens array as an objective optical system is being proposed, for example, in Japanese Patent Application Laid-Open Publication No. 2018-50769 and Japanese Patent Application Laid-Open Publication No. 2010-91986.

Each structure of the layered lens arrays disclosed in Japanese Patent Application Laid-Open Publication No. 2018-50769 and Japanese Patent Application Laid-Open Publication No. 2010-91986 above includes, for example, an optical lens unit configured to allow light from an observation target to pass through and form an optical image of the observation target and a bonding unit for fixing respective optical lenses in an optical axis direction in a region surrounding an outer circumference of the optical lens unit. The structure includes an illumination optical system disposed in a region further on the outer circumference side of the bonding unit.

On the other hand, it is possible to consider a configuration that reduces a diameter of the optical lens unit while securing the bonding unit region in order to achieve a smaller diameter of the layered lens array.

SUMMARY OF THE INVENTION

A wafer lens array according to one aspect of the present invention includes a wafer lens formed by arranging a plurality of plate members on a plane, each plate member including: a first window configured to allow light for forming an optical image to pass through; a light-shielding portion formed on an outer circumferential edge of the first window; and a second window formed on an outer circumferential side of the light-shielding portion and configured to allow illumination light to pass through, wherein the wafer lens in plurality are coaxially layered and the layered wafer lenses are bonded and fixed together in a region of the second window.

A layered lens array according to one aspect of the present invention includes a wafer lens formed by arranging a plurality of plate members on a plane, each plate member including: a first window on which an optical lens configured to allow light for forming an optical image to pass through is disposed; a light-shielding portion formed on an outer circumferential edge of the first window; and a second window formed on an outer circumferential side of the light-shielding portion and configured to allow illumination light to pass through, the wafer lens in plurality being coaxially layered and the layered wafer lenses being bonded and fixed together in a region of the second window, wherein the layered lens array is formed by cutting out the wafer lens array for each predetermined region.

A layered lens array according to another aspect of the present invention includes a plate member including: a first window on which an optical lens configured to allow light for forming an optical image to pass through is disposed; a light-shielding portion formed on an outer circumferential edge of the first window; and a second window formed on an outer circumferential side of the light-shielding portion and configured to allow illumination light to pass through, wherein the plate member in plurality are coaxially layered and the layered plate members are bonded and fixed together in a region of the second window.

An image pickup unit according to one aspect of the present invention includes a layered lens array formed by coaxially layering a plurality of plate members, each plate member including a first window on which an optical lens configured to allow light for forming an optical image to pass through is disposed, a light-shielding portion formed on an outer circumferential edge of the first window and a second window formed on an outer circumferential side of the light-shielding portion and configured to allow illumination light to pass through, the plurality of layered plate members being bonded and fixed together in a region of the second window, and an image pickup device disposed so as to face the first window of the layered lens array and on which the optical image is formed.

A method for manufacturing a layered lens array according to another aspect of the present invention includes forming a wafer lens by arranging a plurality of plate members on a plane, each plate member comprising a first window on which an optical lens configured to allow light for forming an optical image to pass through is disposed, a light-shielding portion formed on an outer circumferential edge of the first window and a second window formed on an outer circumferential side of the light-shielding portion and configured to allow illumination light to pass through; coaxially layering the wafer lens in plurality; forming a wafer lens array by bonding and fixing the layered wafer lenses in a region of the second window; and cutting out the wafer lens array for each predetermined region to provide the layered lens array.

An endoscope according to one aspect of the present invention includes an optical member in which a plurality of plate members are coaxially layered and the plurality of plate members are bonded and fixed in a region of a second window, each plate member comprising: a first window configured to allow light for forming an optical image to pass through; a first light-shielding portion formed on an outer circumference of the first window; and the second window formed on an outer circumferential side of the first light-shielding portion and configured to allow illumination light to pass through; an image pickup device disposed so as to face the first window at a first end of the optical member and on which the optical image is formed; and an illumination member disposed outside in an outer circumferential direction of the image pickup device so as to face the second window at the first end and configured to emit the illumination light.

An endoscope according to another aspect of the present invention includes an optical member in which a plurality of plate members are coaxially layered and the plurality of plate members are fixed, each plate member comprising: a first window configured to allow light for forming an optical image to pass through; a first light-shielding portion formed on an outer circumference of the first window; and a second window formed on an outer circumferential side of the first light-shielding portion and configured to allow illumination light to pass through; an image pickup device disposed so as to face the first window at a first end of the optical member and on which the optical image is formed; an illumination member disposed outside in an outer circumferential direction of the image pickup device so as to face the second window at the first end and configured to emit the illumination light; and a cover member comprising: a third window corresponding to the first window on a second end side, the second end side being an opposite side of the first end; and a second light-shielding portion formed on an inner circumferential edge of the third window and corresponding to the first light-shielding portion, the third window and the second light-shielding portion being disposed at positions facing the second end of the optical member and the cover member being disposed so as to surround an outer circumferential surface of the optical member.

DETAILED DESCRIPTION OF THE PREFERRED EMBODIMENTS

The present invention will be described with embodiments illustrated hereinafter.

Each drawing used in the following description is intended for schematic illustration, and respective components may be shown in different dimensional relationships and scales among respective members so that the respective components are shown in sizes to make them recognizable on the drawings. Therefore, the present invention is not limited to only the illustrated forms with regard to quantities of the components, shapes of the components, size ratios among the components and relative positional relationships among the components described in the respective drawings.

Note that each embodiment, which will be described hereinafter illustrates an example where a layered lens array, which is cut out from a layered wafer lens array, formed using a wafer lens of the present invention is applied as an image pickup optical system and an illumination optical system (light guide unit) of an endoscope.

First Embodiment

Before describing details of a layered lens array according to a first embodiment of the present invention, a schematic configuration of an endoscope to which the layered lens array is applied will be described mainly using FIG. 1 and FIG. 2 first.

Figure 1:
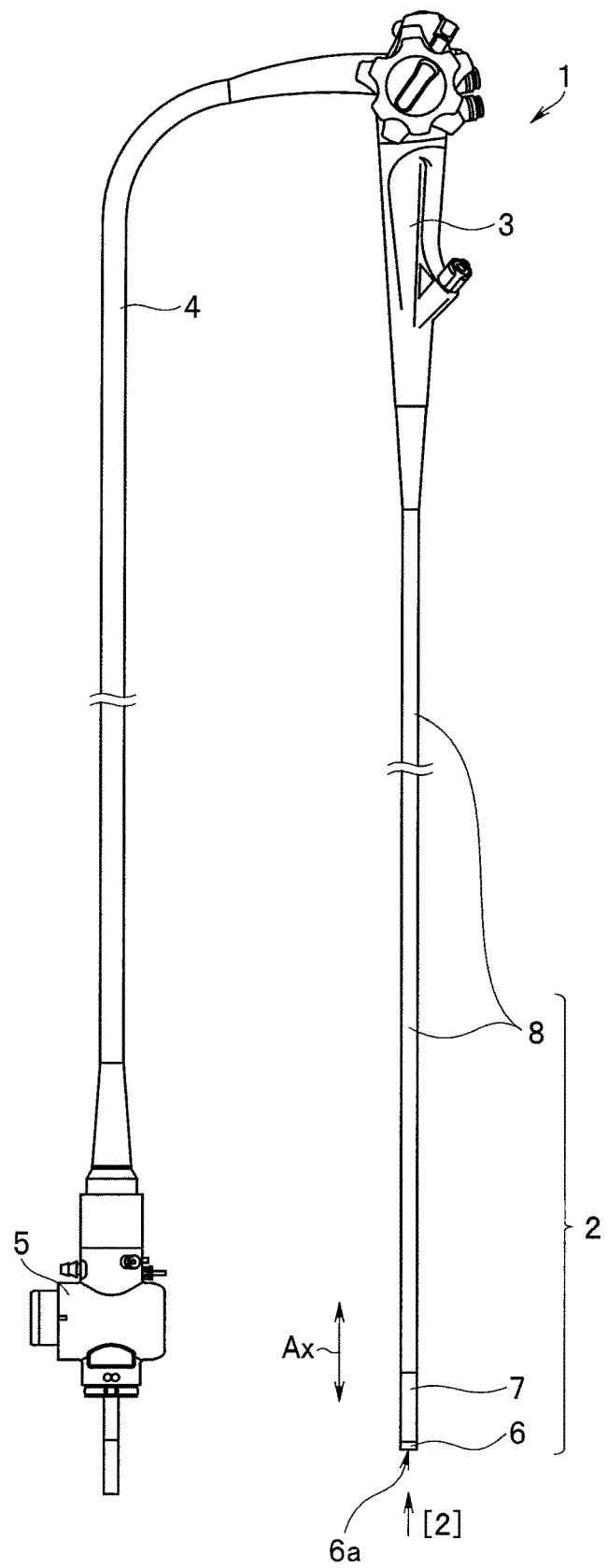
FIG. 1 is an outline view illustrating a schematic configuration of an endoscope to which a layered lens array according to each embodiment of the present invention is applied.
Figure 2:
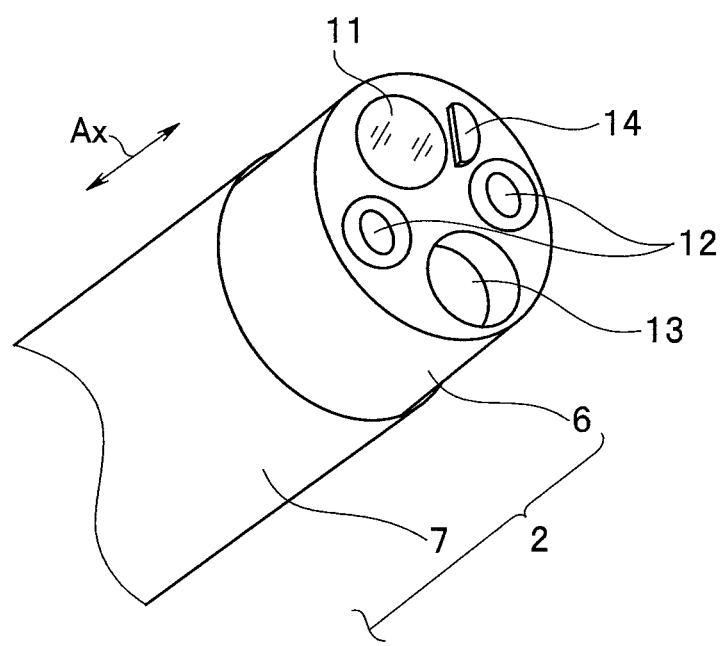
FIG. 2 is an enlarged perspective view of main parts when the distal end portion of the endoscope in FIG. 1 is seen from a direction shown by an arrow [2] in FIG. 1.

FIG. 1 and FIG. 2 are diagrams illustrating a schematic configuration of the endoscope to which the layered lens array according to each embodiment of the present invention is applied. Among these drawings, FIG. 1 is an outline view of the endoscope. FIG. 2 is an enlarged perspective view of main parts when the distal end portion of the endoscope in FIG. 1 is seen from a direction shown by an arrow [2] in FIG. 1.

An endoscope 1 to which the layered lens array according to each embodiment of the present invention is applied mainly includes an insertion portion 2, an operation portion 3, a universal cord 4 and an endoscope connector 5 or the like as illustrated in FIG. 1.

The insertion portion 2 is a tube member formed into an elongated tube shape and inserted into a body cavity of a living body. The insertion portion 2 is formed of a distal end portion 6, a bending portion 7 and a flexible tube unit 8 connected in that order from a distal end side, and is provided with flexibility as a whole.

Among these components, the distal end portion 6 is internally provided with a distal end rigid member and the distal end rigid member incorporates various component units such as an image pickup unit, which is an image pickup apparatus made up of an image pickup optical system, an image pickup device and an image pickup substrate for such a component, a treatment instrument insertion channel, an illumination unit, which is an illumination part or illumination member made up of an illumination optical system and an illumination light guide fiber bundle (none is shown) configured to radiate illumination light forward.

The bending portion 7 is a mechanism unit configured to receive a turning operation of a bending knob to perform bending operation among operation members provided at the operation portion 3 and actively bend part (the bending portion 7) of the insertion portion 2 in up-down, left-right directions.

The flexible tube unit 8 is a tube member formed with flexibility to be passively flexible. Not only a treatment instrument insertion channel but also various electric signal lines extending to the inside of the universal cord 4 from the image pickup unit built in the distal end portion 6 through the operation portion 3, a light guide fiber bundle (not shown) configured to guide light emitted from a light source apparatus, which is an external device to an illumination window 12 (see FIG. 2) provided at a distal end face of the distal end portion 6 or the like are inserted through the flexible tube unit 8.

The operation portion 3 is a constitution unit connected to a proximal end portion of the insertion portion 2 and including a plurality of operation members.

The universal cord 4 is a flexible hollow tube member extending from the operation portion 3. The universal cord 4 is a composite cable through which various electric signal lines extending from the distal end portion 6 of the insertion portion 2, passing through the insertion portion 2 and the operation portion 3, a light guide fiber bundle extending from the light source apparatus (not shown), which is an external device and an air/water feeding tube from an air/water feeding apparatus (not shown), which is an external device, or the like are inserted.

The endoscope connector 5 is a connection member disposed at a distal end of the universal cord 4 and configured to secure connections with external devices. The endoscope connector 5 includes not only an electric connector part (not shown) for connection with a video processor (not shown), which is an external device, but also a light guide bundle for connection with a light source apparatus (not shown), which is an external device, a light source connector part for connecting an electric cable (not shown) that bundles the various electric signal lines and an air/water feeding plug (not shown) for connecting an air/water feeding tube (not shown) from an air/water feeding apparatus (not shown), which is an external device.

As illustrated in FIG. 2, an observation window 11, illumination windows 12, a treatment instrument insertion channel opening 13, and a water feeding nozzle 14 or the like are provided on a distal end face 6a of the distal end portion 6 of the insertion portion 2 of the endoscope 1.

Among these components, the observation window 11 is an opening window provided on a front side of an image pickup optical system (which will be described later) included in the image pickup unit and configured to capture light from an observation target. A transparent flat plate member made of glass or a resin material is fitted in the observation window 11.

The illumination windows 12 are opening windows provided on the front side of the illumination unit (illumination part) and configured to emit light emitted from the light source apparatus and guided by the light guide fiber bundle (not shown) toward the front of the endoscope 1.

The treatment instrument insertion channel opening 13 is a distal end opening of the treatment instrument insertion channel inserted in the insertion portion 2 and is an opening part to allow the distal end side of the treatment instrument inserted in the treatment instrument insertion channel to protrude.

The water feeding nozzle 14 is an ejection port provided at a distal end portion of the air/water feeding tube from the air/water feeding apparatus (not shown) and configured to eject gas or liquid sent out from the air/water feeding apparatus toward an external surface of the observation window 11.

The endoscope 1 illustrated in FIG. 1 is an endoscope, a so-called flexible scope provided with the flexible insertion portion 2. A basic configuration of the endoscope 1 is substantially the same as the configuration of the conventional form generally put in practical use. Therefore, further description of the configuration of the endoscope 1 will be omitted.

Note that directions denoted by an arrow with a reference character Ax in FIG. 1 and FIG. 2 are assumed to be insertion axis directions of the endoscope 1. The direction along the insertion axis Ax is also a direction that substantially coincides with the optical axis of the image pickup optical system of the image pickup unit.

Figure 3:
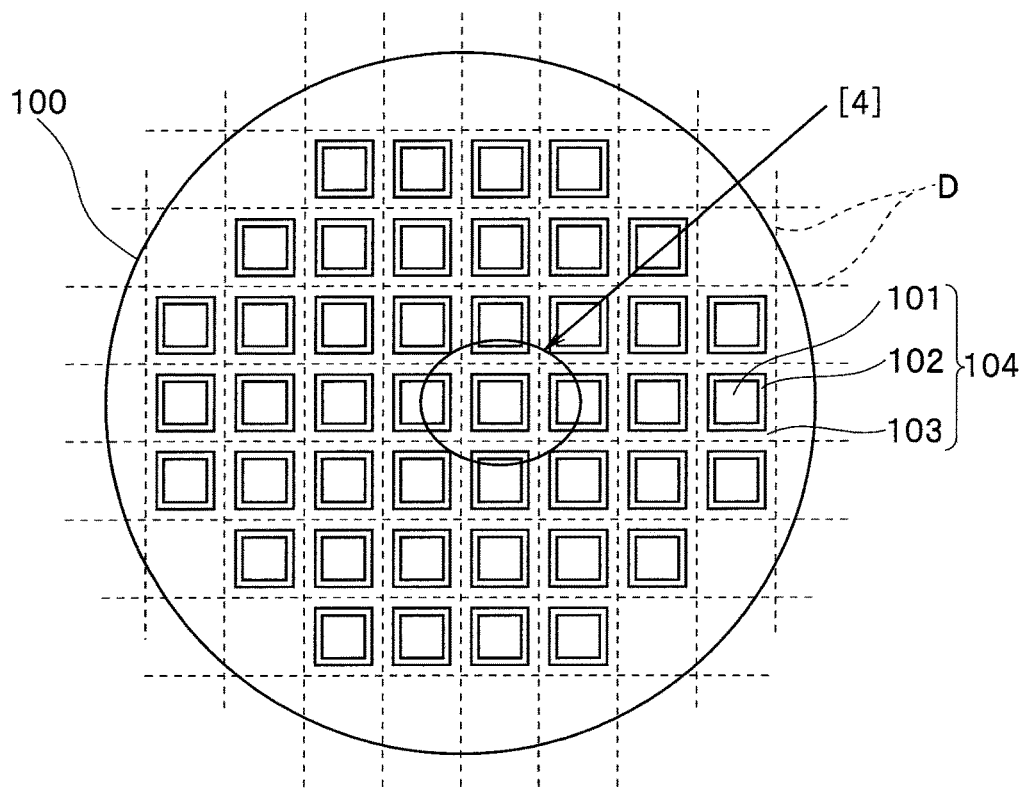
FIG. 3 is a schematic plan view illustrating a schematic configuration of a wafer lens according to a first embodiment of the present invention.
Figure 4:
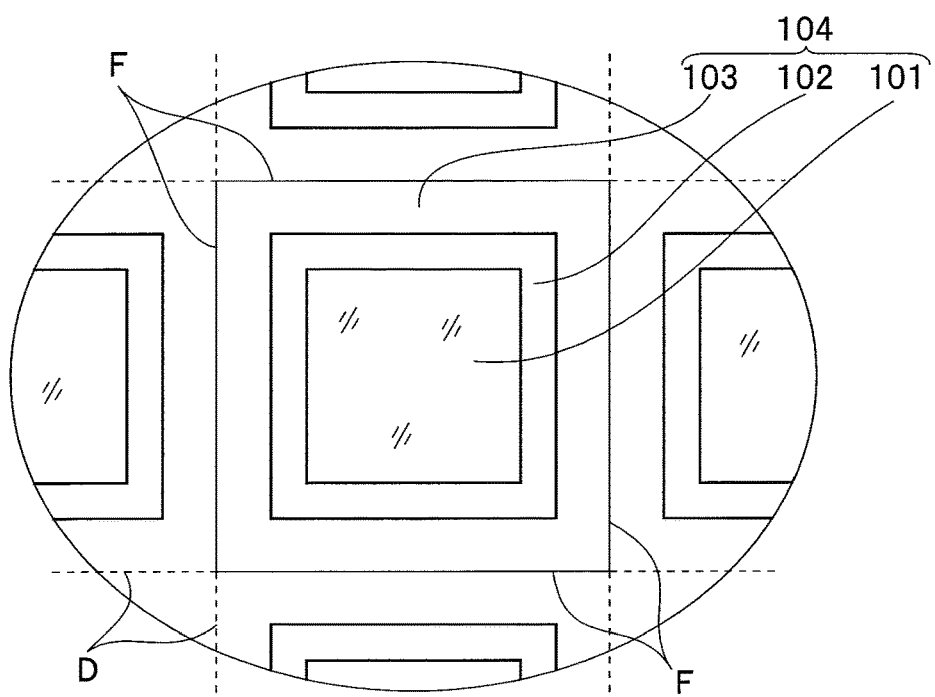
FIG. 4 is an enlarged schematic plan view of main parts illustrating a part (one unit of the plate member) shown by an arrow [4] in FIG. 3.
Figure 5:
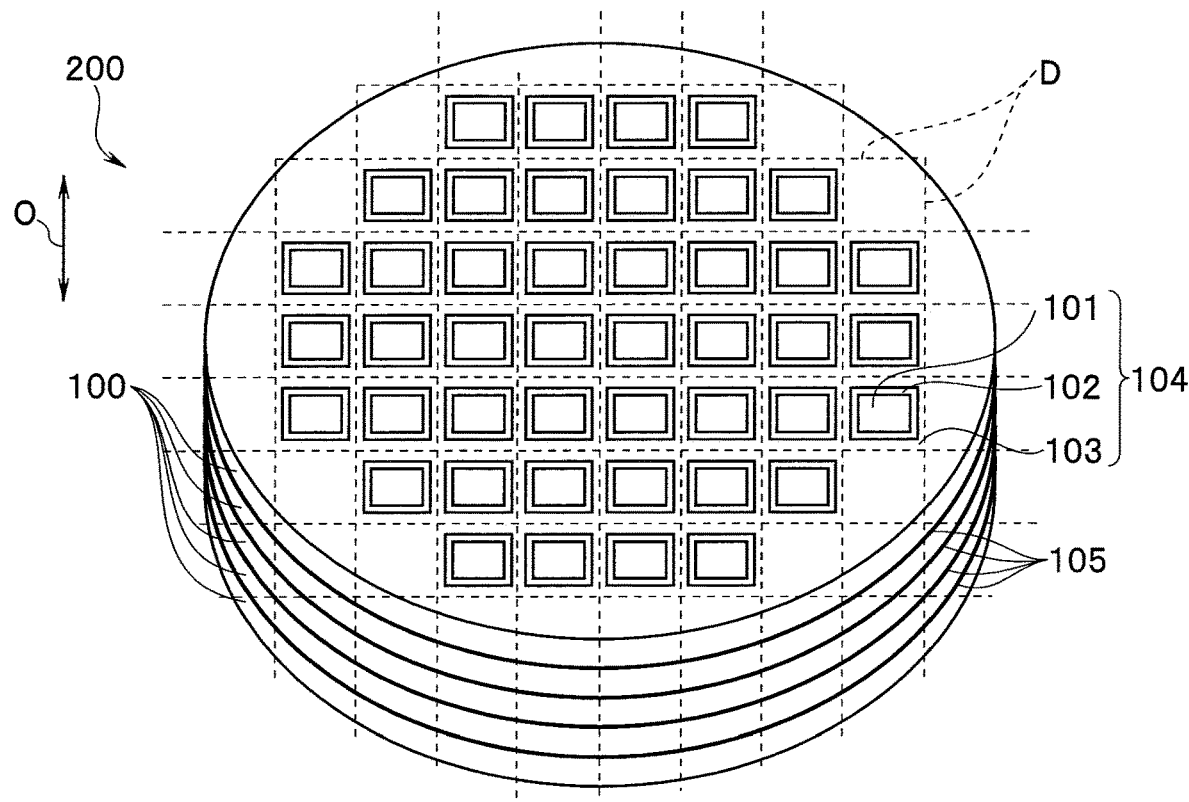
FIG. 5 is a schematic perspective view illustrating a schematic configuration of a wafer lens array formed by coaxially layering a plurality of wafer lenses in FIG. 3.
Figure 6:
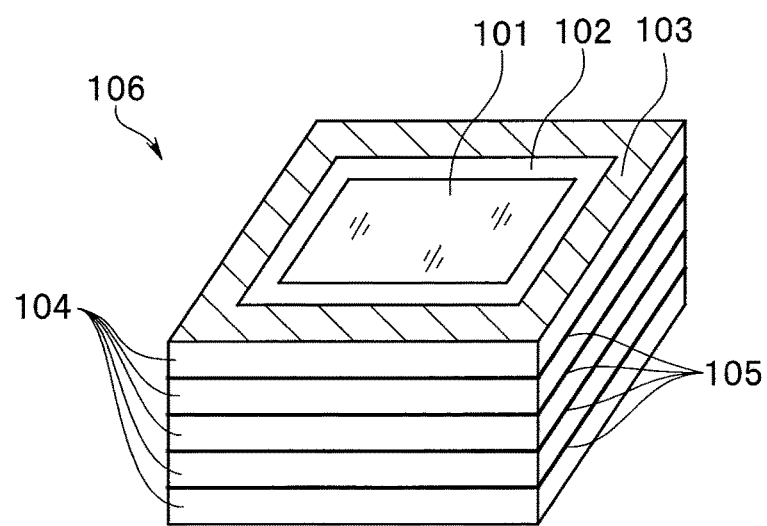
FIG. 6 is an enlarged perspective view illustrating a schematic configuration of a layered lens array according to a first embodiment of the present invention.

Next, the basic configurations of the wafer lens and the layered lens array according to the first embodiment of the present invention will be described below using FIG. 3 to FIG. 6. FIG. 3 is a schematic plan view illustrating a schematic configuration of a wafer lens according to the present embodiment. FIG. 4 is an enlarged schematic plan view of main parts illustrating a part (one unit of the plate member) shown by an arrow [4] in FIG. 3. FIG. 5 is a schematic perspective view illustrating a schematic configuration of a wafer lens array formed by coaxially layering a plurality of wafer lenses in FIG. 3. FIG. 6 is an enlarged perspective view illustrating a schematic configuration of the layered lens array according to the present embodiment.

As illustrated in FIG. 3, a wafer lens 100 of the present embodiment as a whole is formed into a disk shape and is a plate made of transparent glass or a transparent resin material. The wafer lens 100 is formed of a plurality of plate members 104, which are a plurality of optical elements, arranged on a plane. Here, dotted lines D illustrated in FIG. 3 denote each region of the plate member 104 and the dotted lines D substantially coincide with dicing lines, which will be described later. In other words, a rectangular region denoted by a reference character F in FIG. 4 is assumed to be one unit of the plate member 104.

The one unit of the plate member 104 includes a first window 101, a first light-shielding portion 102 and a second window 103.

The first window 101 is an opening including an optical lens unit configured to allow light from an observation target to pass through and form an optical image of the observation target. For this reason, the first window 101 is made of transparent glass or a transparent resin material.

The first light-shielding portion 102 is a light-shielding portion configured to shield light incident from the outside of the first window 101 on the inside of the first window 101. Thus, the first light-shielding portion 102 is made of, for example, a black resin material formed on an outer circumferential edge of the first window 101 so as to surround the outer circumference of the first window 101.

The second window 103 is formed on an outer circumferential side of the first light-shielding portion 102 and made of transparent glass or a transparent resin material so as to allow illumination light, which will be described later, to pass through.

The wafer lens 100 of this form is made of transparent glass or a transparent resin material as a whole and the region of the first light-shielding portion 102 is formed by, for example, two-color molding or insert molding.

The plurality of wafer lenses 100 thus formed are coaxially layered in a direction indicated by an arrow O in FIG. 5 and a layered wafer lens array 200 is thereby formed as illustrated in FIG. 5. At this time, the plurality of first windows 101 and the plurality of first light-shielding portions 102 of the respective wafer lenses 100 are arranged so as to substantially coincide with one another in a direction along the optical axis O. Note that FIG. 5 illustrates a form in which five wafer lenses 100 are coaxially layered.

Note that in this case, a transparent adhesive 105 made of a light transmission material through which illumination light can pass is applied to a region of the second window 103 where surfaces of the respective wafer lenses 100 face each other. The respective opposing wafer lenses 100 are fixed in the arrow O direction by the action of the transparent adhesive 105 and the layered wafer lens array 200 is thereby formed.

The layered wafer lens array 200 formed in this way is subjected to dicing processing for each predetermined region (that is, for each unit of the plate member 104) along dotted lines D in FIG. 5 and a layered lens array 106, which is a plurality of layered optical members, is cut out.

The layered lens array 106 cut out in this way is formed as a lens array in the form in which a plurality of (5 in this example) plate members 104 are coaxially layered in the arrow O direction, that is, in the optical axis direction of the optical lens unit that forms the first window 101 as illustrated in FIG. 6.

Note that a region indicated by diagonal lines in FIG. 6 is the second window 103. The transparent adhesive 105 is applied to a part (see a reference numeral 105 illustrated in FIG. 6) where the plurality of plate members 104 face each other in the region indicated by diagonal lines corresponding to the second window 103. Therefore, the layered lens array 106 is configured to allow light to pass through in the arrow O direction in the respective regions of the first window 101 and the second window 103.

On the other hand, the first light-shielding portion 102 prevents light passing through the second window 103 from entering the first window 101. Similarly, the first light-shielding portion 102 is also configured to prevent light from emitting or entering from the first window 101 side to the second window 103 side.

The mode in which the layered lens array 106 of the present embodiment thus formed is applied as the image pickup optical system and the illumination optical system (light guide unit) of the endoscope 1 will be described using FIG. 7 and FIG. 8.

Figure 7:
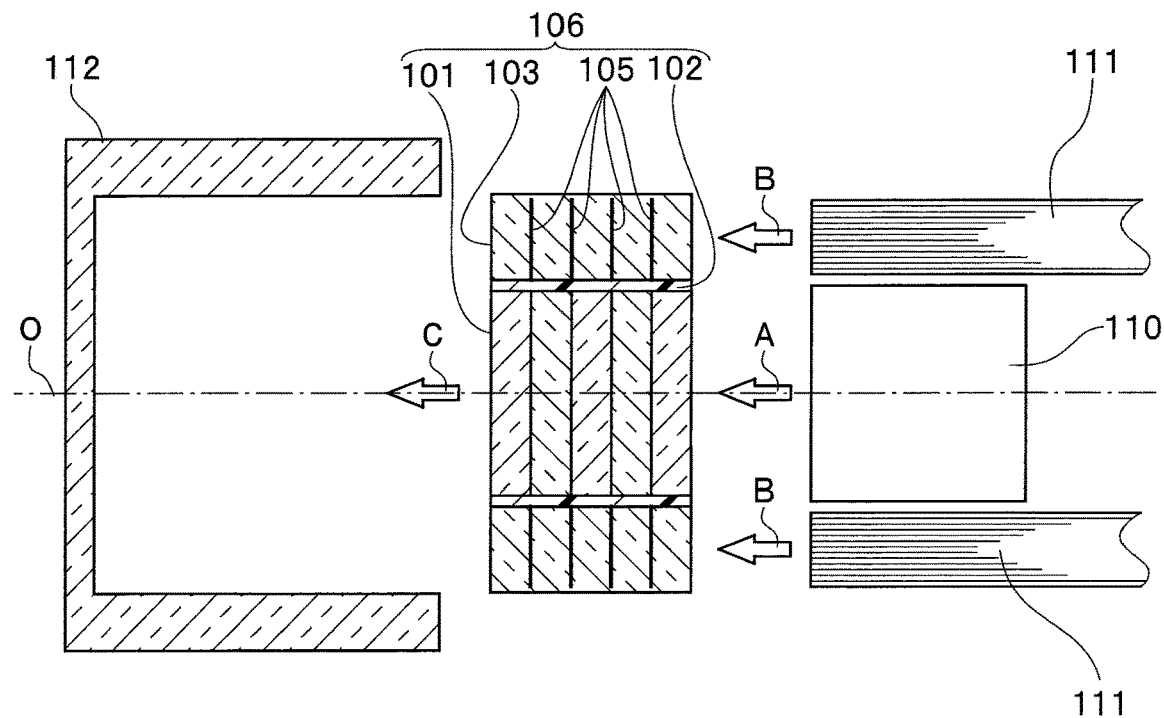
FIG. 7 is an exploded view of main parts illustrating a configuration example when the layered lens array according to the first embodiment of the present invention is applied to an endoscope.
Figure 8:
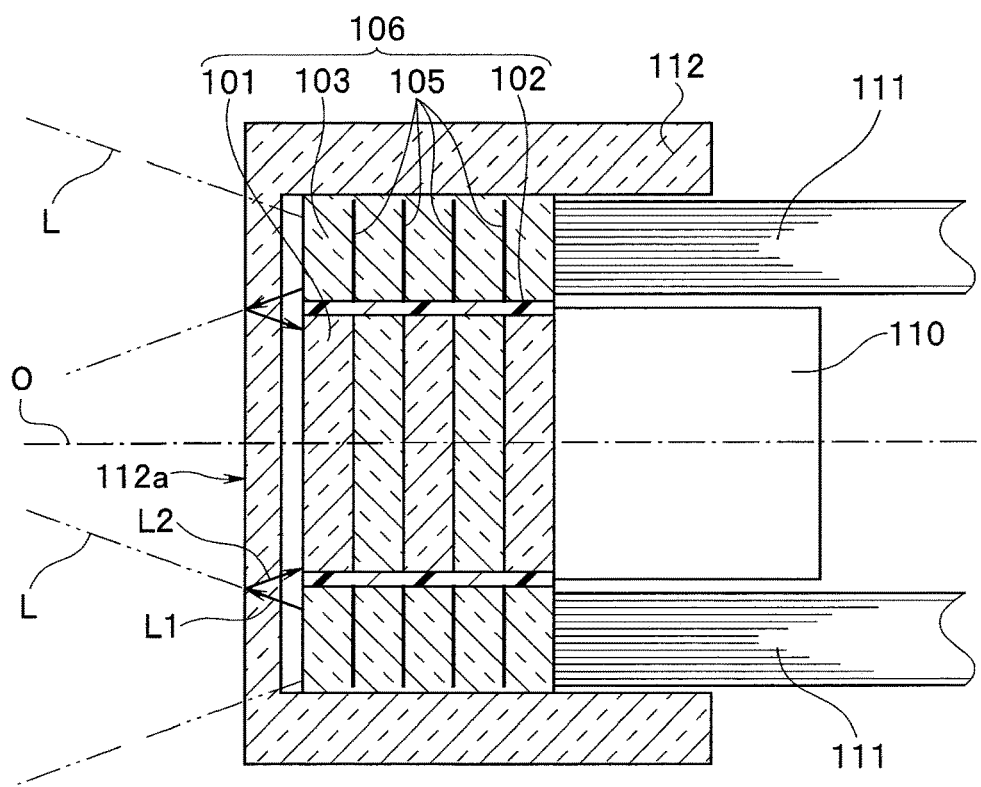
FIG. 8 is an assembly diagram of FIG. 7.

FIG. 7 and FIG. 8 are diagrams illustrating a configuration example when the layered lens array according to the present embodiment is applied to an endoscope. Among these drawings, FIG. 7 is an exploded view of main parts and FIG. 8 is an assembly diagram.

When the layered lens array 106 of the present embodiment is applied as the image pickup optical system and the illumination optical system (light guide unit) of the endoscope 1, the following configuration is adopted.

Note that it is assumed in the following description that the optical axis of the optical lens unit of the first window 101 of the layered lens array 106 is denoted by a reference character O. In the layered lens array 106, the surface facing the proximal end side of the insertion portion 2 of the endoscope 1 will be referred to as a "first end face" or a "first end." On the other hand, the surface opposite to the first end face of the layered lens array 106 in a direction along the optical axis O (that is, the surface facing the distal end of the insertion portion 2 of the endoscope 1) will be referred to as a "second end face" or a "second end."

As illustrated in FIG. 7, an image pickup section 110, which is an image pickup device, that constitutes part of the image pickup unit is disposed at a position facing the first end face of the first window 101 of the layered lens array 106 (see an arrow denoted by a reference character [A] in FIG. 7). More specifically, a light receiving surface of the image pickup device included in the image pickup section 110 is disposed so as to face the first end face of the first window 101.

Similarly, an illumination light guide fiber bundle 111 of the illumination unit (illumination part) is disposed on the first end face of each second window 103 of the layered lens array 106 (see an arrow denoted by a reference character [B] in FIG. 7). In this case, the illumination light guide fiber bundle 111 is disposed on an outside in an outer circumferential direction of the image pickup section 110. A front surface of the illumination light guide fiber bundle 111, that is, an emission surface of the illumination light is disposed so as to face the first end face of the second window 103.

With such a configuration, the layered lens array 106 functions as an image pickup optical system and an illumination optical system (light guide unit).

A cover member 112 is disposed on an outer surface side of the layered lens array 106 with the image pickup section 110 and the illumination light guide fiber bundle 111 assembled (see an arrow denoted by a reference character [C] in FIG. 7 and see FIG. 8). The cover member 112 is formed so as to cover, for example, the front surface (second end face) of the layered lens array 106 and an outer circumferential surface in a diameter direction (direction orthogonal to the optical axis O; outer circumferential direction). The cover member 112 is made of a transparent resin material or the like.

FIG. 8 illustrates a state in which the layered lens array 106, the image pickup section 110, the illumination light guide fiber bundle 111 and the cover member 112 are assembled in a predetermined form. The constitution units in this state are disposed at predetermined positions inside the distal end rigid member of the distal end portion 6 of the endoscope 1.

The rest of the configuration as the endoscope 1 is substantially the same as the configuration of endoscopes conventionally and generally put to practical use.

As described above, the wafer lens 100 according to the above first embodiment is formed by arranging a plurality of plate members 104 on a plane, each plate member 104 including the first window 101 including an optical lens unit and configured to allow light to pass through and form an optical image, a first light-shielding portion 102 formed on an outer circumferential edge of the first window 101 and a second window 103 formed on an outer circumferential side of the first light-shielding portion 102 and configured to allow illumination light to pass through. In this case, since the first window 101 and the second window 103 to allow light to pass through and the first light-shielding portion 102 to shield light between the first window 101 and the second window 103 are formed on the single wafer lens 100 by two-color molding or insert molding, it is possible to contribute to a cost reduction.

The layered lens array 106 of the present embodiment is a layered optical member formed by coaxially layering a plurality of wafer lenses 100, applying a transparent adhesive 105 configured to allow illumination light to pass through between the opposing second windows 103, fixing the plurality of wafer lenses 100 to form the layered wafer lens array 200 and cutting out (dicing) the layered wafer lens array 200 into a plurality of pieces for each predetermined region (plate member 104). Note that the first light-shielding portion 102 may be made of an adhesive material to fix the plurality of wafer lenses 100 using the adhesiveness of this material.

This configuration allows the second windows 103 of the plurality of coaxially layered wafer lenses 100 to be formed so as to allow illumination light to pass through.

Therefore, with this configuration, it is possible to effectively use the region corresponding to a bonded part, which cannot be used in the layered lens array of a conventional structure, resulting in an unnecessary region, that is, the region of the second window 103 in the present embodiment, as the light guide unit of the illumination optical system. At the same time, it is possible to reduce the outer diameter of the layered lens array 106 by an amount corresponding to the region of the bonded part.

The endoscope 1 of the present embodiment uses the above layered lens array 106 as the light guide unit for the image pickup optical system and the illumination optical system. In other words, a light receiving surface of the image pickup section 110 is disposed at a position facing the first window 101 at one end of the layered lens array 106, an illumination unit (illumination light guide fiber bundle 111) is disposed outside in the outer circumferential direction of the image pickup section 110 and an emission surface of illumination light in the illumination unit (illumination light guide fiber bundle 111) is disposed at a position facing the second window 103 at one end of the layered lens array 106.

With such a configuration, the above layered lens array 106 is applied as the light guide unit for the image pickup optical system and the illumination optical system in the endoscope 1, and it is thereby possible to contribute to a reduction of diameter of the distal end portion 6 of the endoscope 1.

More specifically, since a configuration that effectively uses the second window 103 as the light guide unit for the illumination optical system is adopted, it is not necessary to provide the illumination light guide fiber bundle 111 up to the distalmost end portion. Therefore, such a configuration can contribute to further reduction of diameter of the distal end portion 6 of the endoscope 1.

Second Embodiment

The endoscope 1 of the aforementioned first embodiment is configured such that illumination light that has transmitted through the illumination light guide fiber bundle 111 is emitted forward from the front surface of the second window 103 via the second window 103 of the layered lens array 106 as illustrated in FIG. 8.

In this case, according to the configuration of the endoscope 1 of the aforementioned first embodiment, the front surface (second end face) of the layered lens array 106 including the second window 103 is covered with the cover member 112. Since the cover member 112 is made of a transparent resin material or the like, illumination light emitted from the second window 103 is radiated forward after passing through the cover member 112.

At this time, depending on the situation, for example, emitted light indicated by an arrow L1 in FIG. 8 may be reflected by a front surface 112a of the cover member 112 and become harmful light (flare) incident on the first window 101 as indicated by an arrow L2 in FIG. 8.

Figure 9:
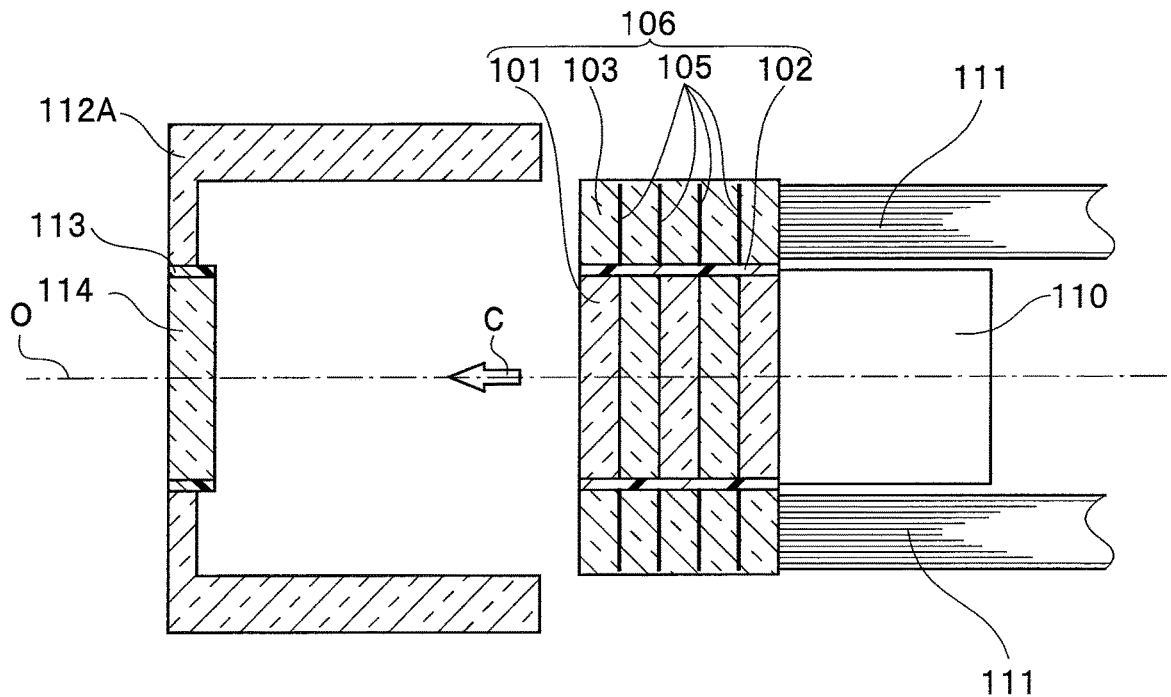
FIG. 9 is an exploded view of main parts illustrating a configuration example of an endoscope according to a second embodiment of the present invention.
Figure 10:
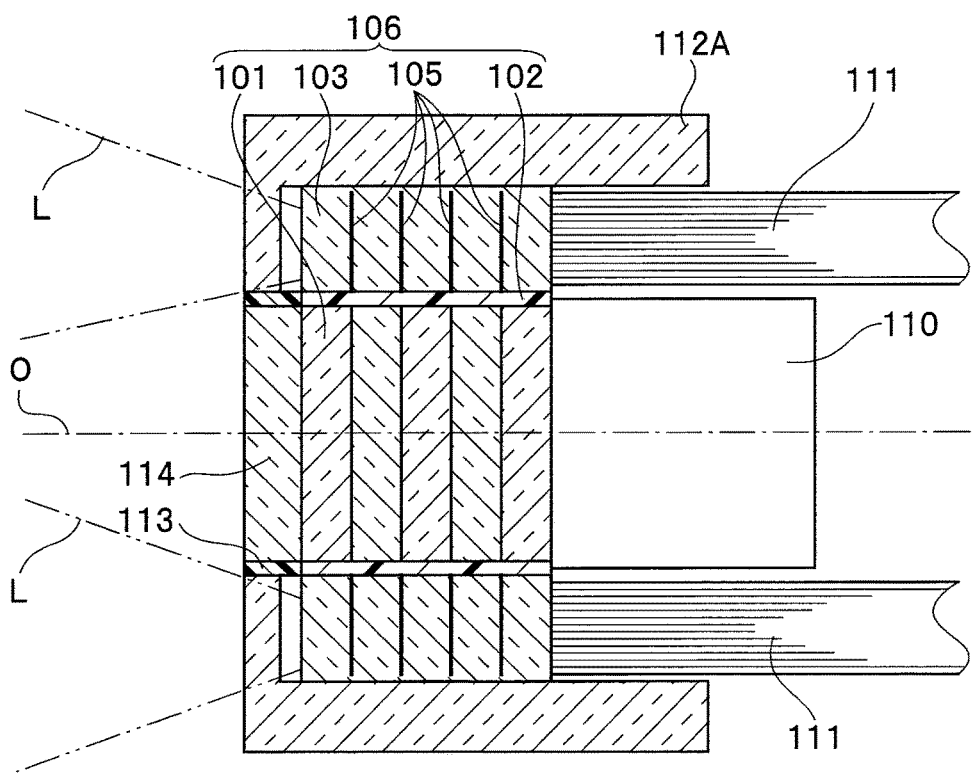
FIG. 10 is an assembly diagram of FIG. 9.

Thus, a second embodiment of the present invention proposes a configuration that prevents such harmful light (flare). FIG. 9 and FIG. 10 are diagrams illustrating a configuration example of an endoscope according to the second embodiment of the present invention. Among these drawings, FIG. 9 is an exploded view of main parts and FIG. 10 is an assembly diagram.

A basic configuration of the present embodiment is substantially the same as the configuration of the aforementioned first embodiment. In other words, the endoscope of the present embodiment is completely the same in that the same layered lens array 106 described in the aforementioned first embodiment is applied as the light guide unit for the image pickup optical system and the illumination optical system of the endoscope.

On the other hand, the present embodiment is different in a configuration of a cover member 112A that holds and covers the layered lens array 106. The rest of the configuration is similar to the configuration of the aforementioned first embodiment. Therefore, in the following description, only different parts will be described in detail.

In the endoscope of the present embodiment, the cover member 112A is configured to include a third window 114 and a second light-shielding portion 113.

Here, the third window 114 is provided at a position corresponding to the first window 101 on the second end face side of the layered lens array 106. The third window 114 is made of transparent glass or a transparent resin material.

The second light-shielding portion 113 is a light-shielding portion formed on an inner circumferential edge of the third window 114 and corresponding to the first light-shielding portion 102. The second light-shielding portion 113 is the light-shielding portion configured to shield illumination light emitted from the second window 103 from entering from the front surface of the first window 101. For that reason, the second light-shielding portion 113 is made of, for example, a black resin material.

The third window 114 and the second light-shielding portion 113 are disposed at positions facing the front surface (second end face) of the layered lens array 106 (optical member). The cover member 112A is disposed so as to surround the outer circumferential surface of the layered lens array 106 (optical member). At the same time, the cover member 112A is disposed so as to cover the front surface of the second window 103. The rest of the configuration is substantially the same as the configuration of the aforementioned first embodiment.

As described above, according to the above second embodiment, it is possible to obtain effects similar to the effects of the aforementioned first embodiment. Furthermore, according to the present embodiment, it is possible to prevent illumination light emitted forward from the second window 103 from being reflected by the front surface of the cover member 112A and entering from the first window 101 as return light. Therefore, it is possible to prevent harmful light (flare) and acquire better images.

Third Embodiment

Although an example has been described in the aforementioned second embodiment where the cover member 112A is provided with the second light-shielding portion 113 and the third window 114 for preventing harmful light (flare), the configuration to prevent flare is not limited to this example. A third embodiment that will be described next is another configuration example of the configuration to prevent flare.

Figure 11:
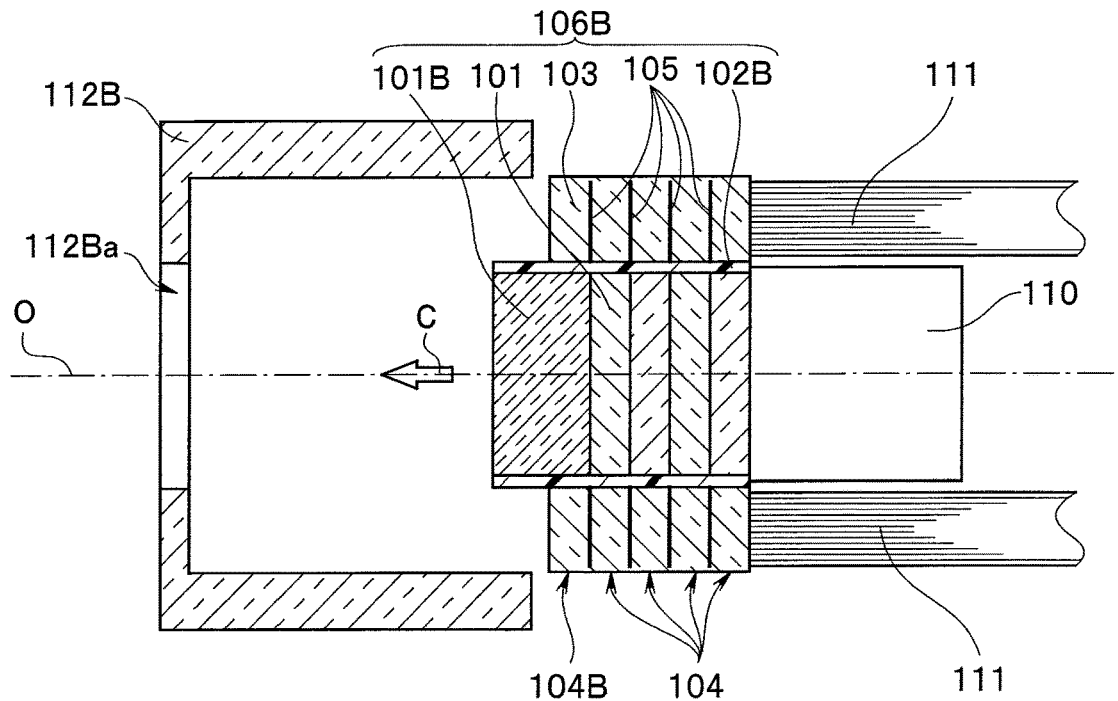
FIG. 11 is an exploded view of main parts illustrating a configuration example of an endoscope according to a third embodiment of the present invention.
Figure 12:
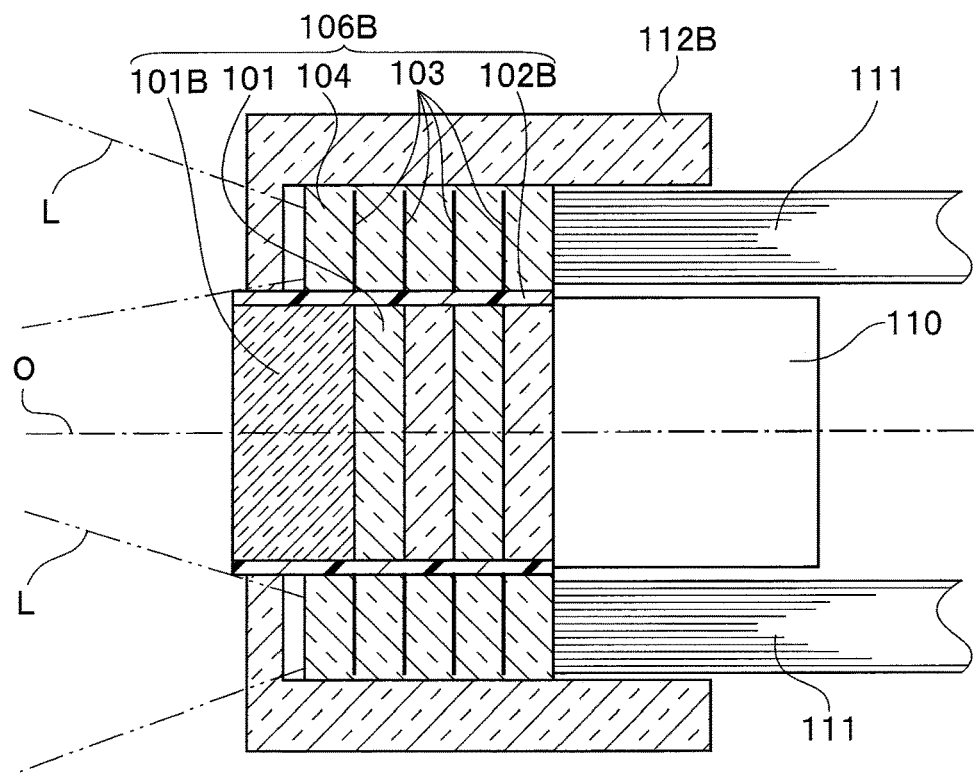
FIG. 12 is an assembly diagram of FIG. 11.

FIG. 11 and FIG. 12 are diagrams illustrating a configuration example of an endoscope according to the third embodiment of the present invention. Among these drawings, FIG. 11 is an exploded view of main parts and FIG. 12 is an assembly diagram.

A basic configuration of the present embodiment is substantially the same as the configurations of the aforementioned first and second embodiments. The endoscope of the present embodiment is slightly different in a configuration of a layered lens array 106B, which is a layered optical member and also slightly different in a configuration of a cover member 112B that covers and holds the layered lens array 106B. The rest of the configuration is substantially the same as the configurations of the aforementioned first and second embodiments. Therefore, in the following description, only different parts will be described in detail.

The layered lens array 106B applied to the endoscope of the present embodiment is formed by coaxially layering a plurality of plate members (104B, 104) in a direction along the optical axis O as illustrated in FIG. 11.

In this case, the plate member 104B at a distalmost end (second end) of the layered lens array 106B is formed by providing a fourth window 101B at a part corresponding to the first window. The fourth window 101B is configured in a form different from the first windows 101 of the other plate members 104.

In other words, the fourth window 101B is disposed at a position facing the first window 101 closer to the other end of the layered lens array 106B (optical member), that is, the distalmost end.

More specifically, the fourth window 101B is formed using a member having higher chemical resistance or a member having higher rigidity than the first window 101. The fourth window 101B is an optical lens unit (objective lens) provided at a distalmost end of the layered lens array 106B. The fourth window 101B is disposed so as to be exposed to the outside from the distal end face of the cover member 112B as will be described later. Therefore, the fourth window 101B is preferably configured to have excellent chemical resistance and scratch-resistant nature. Therefore, the fourth window 101B at the distalmost end is made of a member having high chemical resistance and a member having high rigidity. Note that a rigid optical element such as sapphire glass is used as the member having high rigidity.

The fourth window 101B is formed so as to have a larger thickness than the other first windows 101 as illustrated in FIG. 11 or the like and is formed so as to slightly protrude forward from the front surface of the second window 103 of the plate member 104B.

The first light-shielding portion 102B is also disposed so as to extend according to the amount of protrusion of the fourth window 101B and is disposed so as to surround the outer circumference of the fourth window 101B. Therefore, the first light-shielding portion 102B is also formed so as to slightly protrude from the front surface of the second window 103 of the plate member 104B.

In order to form the plate member 104B of such a form, for example, when molding a wafer lens, it is possible to form the plate member 104B using a procedure of leaving the portion corresponding to the fourth window 101B as a cavity, molding the other parts (the first light-shielding portion 102B and the second window 103) and then fitting the optical lens unit formed separately in advance into the cavity corresponding to the fourth window 101B in accordance with the fourth window 101B.

Note that as another procedure, when molding, for example, a wafer lens, it is also possible to employ a procedure of molding by including the optical lens unit of a high rigidity member in the part corresponding to the fourth window 101B.

On the other hand, when the layered lens array 106B is assembled (state in FIG. 12), the cover member 112B is formed so as to include an opening 112Ba in which the fourth window 101B is fitted at a region facing the fourth window 101B at the other end (distal end) of the layered lens array 106B (optical member).

With such a configuration, when the layered lens array 106B is assembled into the cover member 112B, the fourth window 101B is exposed from the distal end face of the cover member 112B.

Note that FIG. 12 illustrates a state in which the distal end faces of the fourth window 101B and the first light-shielding portion 102B slightly protrude from the distal end face of the cover member 112B, but the present invention is not limited to this form. For example, the distal end faces of the fourth window 101B and the first light-shielding portion 102B may be configured to be substantially flush with the distal end face of the cover member 112B. The rest of the configuration is substantially the same as the configurations of the aforementioned respective embodiments.

As described above, according to the above third embodiment thus formed, it is possible to obtain effects similar to the effects of the aforementioned respective embodiments. Furthermore, according to the present embodiment, since the fourth window 101B at the distalmost end of the layered lens array 106B is made of a member having higher chemical resistance or a member having higher rigidity than the first window 101, it is possible to provide a configuration with excellent chemical resistance or a scratch-resistant configuration. Therefore, even when the fourth window 101B is exposed from the distal end face of the cover member 112B, scratch-resistance with respect to the fourth window 101B is secured, and it is thereby possible to perform observation without any problem.

Unlike the aforementioned respective embodiments, there is no member constituting the cover member 112B on the front surface side of the fourth window 101B, and so it is possible to prevent harmful light (flare).

Furthermore, the fourth window 101B is configured such that the first light-shielding portion 102B is disposed so as to extend up to the protruding portion. This configuration prevents the occurrence of harmful light (flare) due to illumination light emitted forward from the second window 103, and can thereby acquire better images.

Fourth Embodiment

A configuration example has been presented in the aforementioned third embodiment where the opening 112Ba is formed in the region corresponding to the fourth window 101B on the front surface of the cover member 112B, the fourth window 101B is fitted into the opening 112Ba and disposed so that the front surface of the fourth window 101B is exposed from the distal end face of the cover member 112B.

A fourth embodiment, which will be described next illustrates a configuration in which not only the first window of a layered lens array but also the second window is exposed from the distal end face of the cover member.

Figure 13:
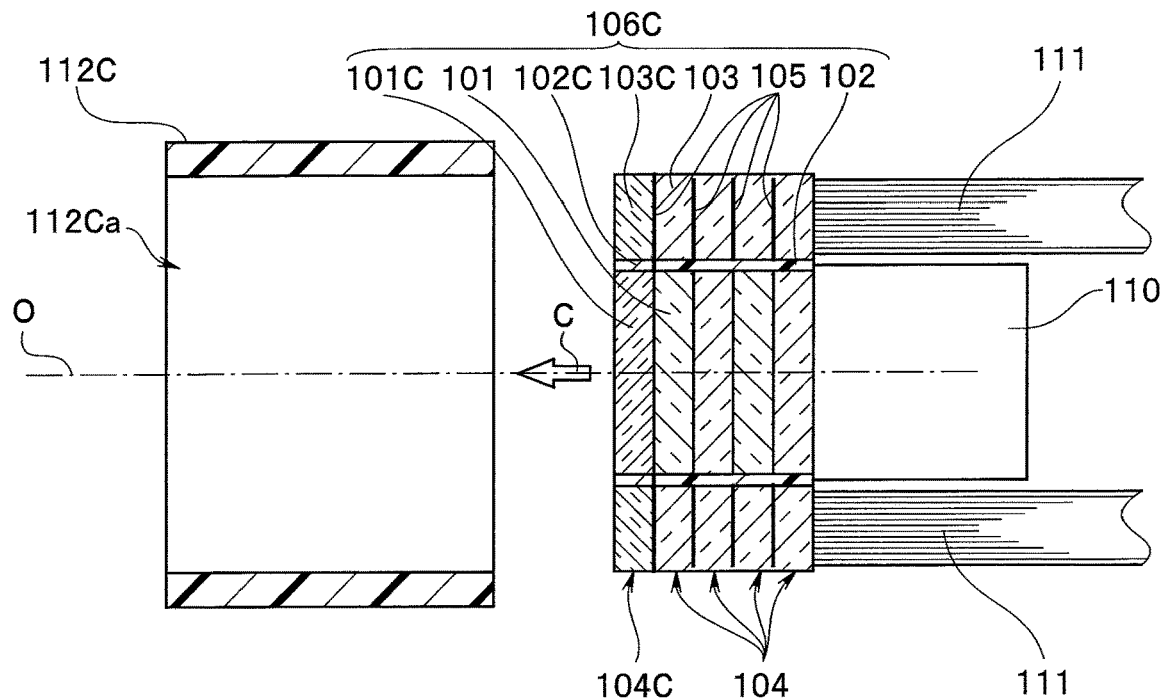
FIG. 13 is an exploded view of main parts illustrating a configuration example of an endoscope according to a fourth embodiment of the present invention.
Figure 14:
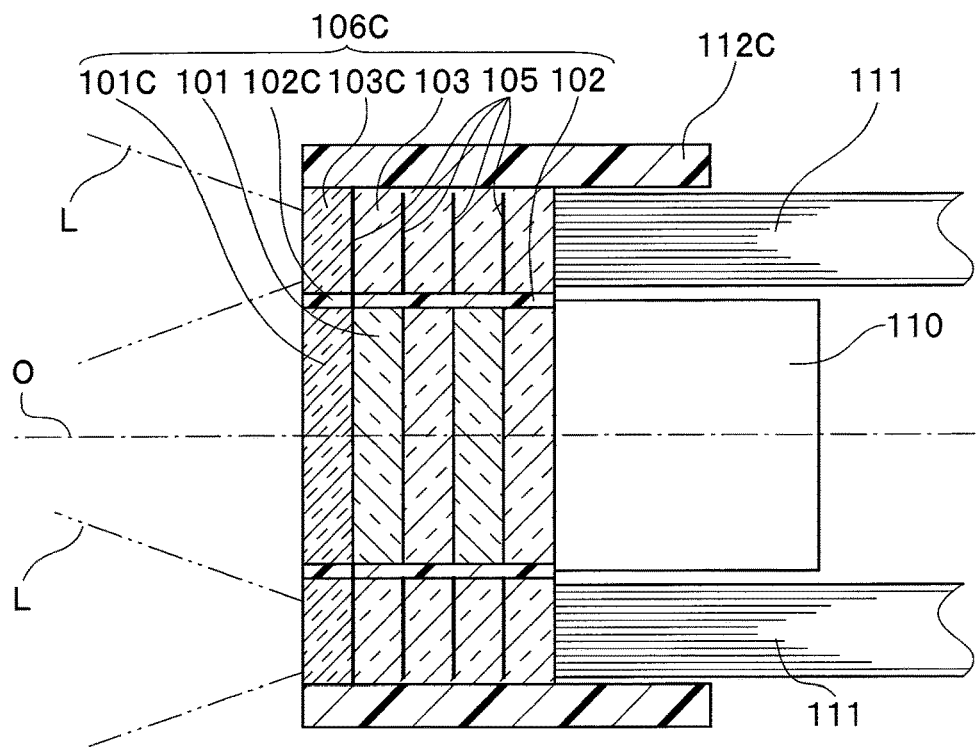
FIG. 14 is an assembly diagram of FIG. 13.

FIG. 13 and FIG. 14 are diagrams illustrating a configuration example of an endoscope according to the fourth embodiment of the present invention. Among these drawings, FIG. 13 is an exploded view of main parts and FIG. 14 is an assembly diagram.

A basic configuration of the present embodiment is substantially the same as the configurations of the aforementioned respective embodiments. The endoscope of the present embodiment is slightly different in a configuration of a layered lens array 106C, which is a layered optical member and also slightly different in a configuration of a cover member 112C that covers and holds the layered lens array 106C. The rest of the configuration is substantially the same as the configurations of the aforementioned respective embodiments. Therefore, in the following description, only different parts will be described in detail.

The layered lens array 106C applied to the endoscope of the present embodiment is formed by coaxially layering a plurality of plate members (104C, 104) in a direction along the optical axis O as illustrated in FIG. 13.

In this case, the plate member 104C at a distalmost end (second end) of the layered lens array 106C is formed by providing a fifth window 101C at a part corresponding to the first window. The fifth window 101C is configured in a form different from the first windows 101 of the other plate members 104.

More specifically, the fifth window 101C is formed using a member having higher chemical resistance or a member having higher rigidity than the first window 101. The fifth window 101C is an optical lens unit (objective lens) provided at a distalmost end of the layered lens array 106C. The fifth window 101C is disposed so as to be exposed to the outside from the distal end of the cover member 112C as will be described later. Therefore, the fifth window 101C is preferably configured to have excellent chemical resistance and scratch-resistant nature. Therefore, the fifth window 101C at the distalmost end is made of a member having high chemical resistance and a member having high rigidity.

Similarly, the plate member 104C at a distalmost end (second end) of the layered lens array 106C is formed by providing a sixth window 103C at a part corresponding to the second window. The sixth window 103C is configured in a form different from the second windows 103 of the other plate members 104.

The sixth window 103C is made of a member having higher chemical resistance or a member having higher rigidity than the second window 103. The sixth window 103C is an illumination optical system provided at the distalmost end of the layered lens array 106C. The sixth window 103C is disposed so as to be exposed to the outside from the distal end of the cover member 112C as will be described later. Therefore, the sixth window 103C is also preferably configured to have excellent chemical resistance and scratch-resistant nature. Therefore, the sixth window 103C at the distalmost end is also made of a member having high chemical resistance and a member having high rigidity.

A third light-shielding portion 102C corresponding to the first light-shielding portion 102 is formed in a region on an outer circumference of the fifth window 101C and between the fifth window 101C and the sixth window 103C.

In order to form the plate member 104C of such a form, for example, when molding a wafer lens, it is possible to form the plate member 104C using a procedure of leaving the portion corresponding to the fifth window 101C and the portion corresponding to the sixth window 103C as cavities, molding the other part (the third light-shielding portion 102C) and then fitting the optical lens unit formed separately in advance into the cavity corresponding to the fifth window 101C in accordance with the fifth window 101C and likewise fitting the illumination optical system formed separately in advance into the cavity corresponding to the sixth window 103C in accordance with the sixth window 103C.

Note that as another procedure, for example, when molding a wafer lens, it is also possible to use a procedure of molding the wafer lens by including the optical lens unit of a high chemical resistance member and a high rigidity member in the parts corresponding to the fifth window 101C and the sixth window 103C.

On the other hand, the cover member 112C is a distal end exterior member formed into a substantially cylindrical shape using a non-transparent member so as to cover the outer circumference of the layered lens array 106C. Therefore, an opening 112Ca is formed in the cover member 112C so that the distal end (second end) of the layered lens array 106C (optical member) is exposed to the outside when the layered lens array 106C is assembled (state in FIG. 14). This configuration causes the fifth window 101C and the sixth window 103C to be exposed from the distal end of the cover member 112C when the layered lens array 106C is assembled into the cover member 112C. The rest of the configuration is substantially the same as the configurations of the aforementioned respective embodiments.

As described above, according to the above fourth embodiment in such a configuration, it is possible to obtain effects similar to the effects of the aforementioned respective embodiments. Furthermore, according to the present embodiment, since the sixth window 103C at the distalmost end of the layered lens array 106C is made of a member having higher chemical resistance or a member having higher rigidity than the second window 103, it is possible to provide a configuration with excellent chemical resistance or scratch resistance. Therefore, even in the form in which the sixth window 103C is exposed from the distal end face of the cover member 112C, chemical resistance or scratch resistance with respect to the sixth window 103C is secured, and it is thereby possible to perform observation without any problem.

Fifth Embodiment

Figure 15:
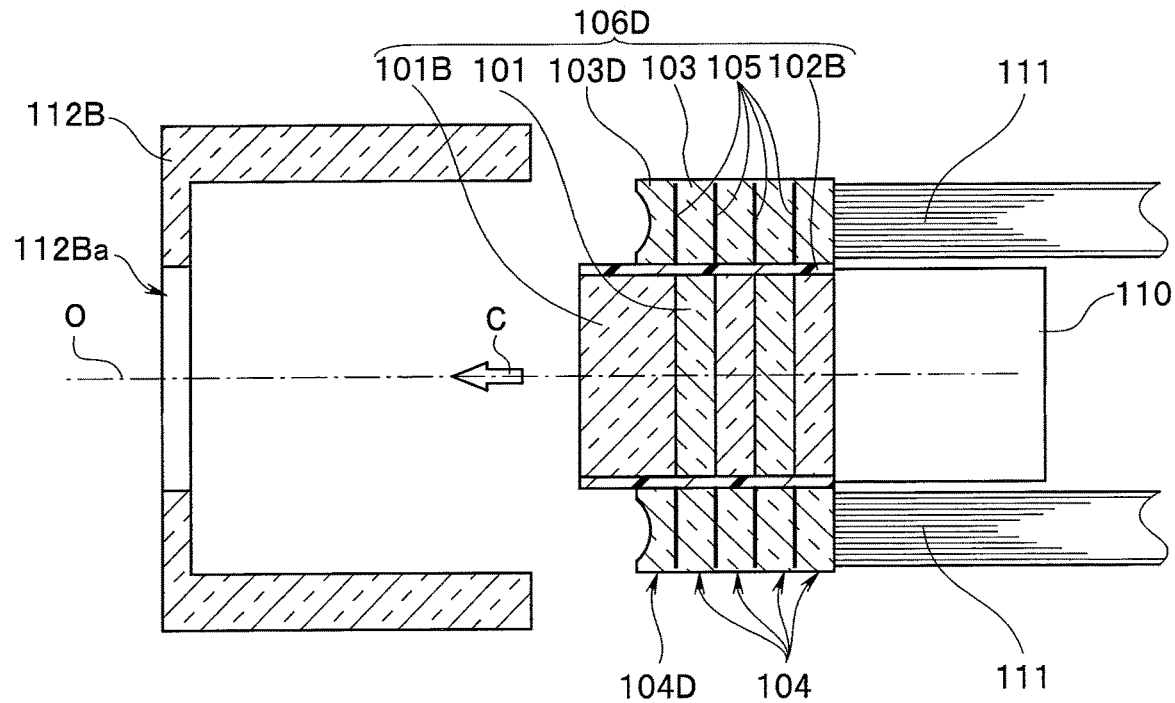
FIG. 15 is an exploded view of main parts illustrating a configuration example of an endoscope according to a fifth embodiment of the present invention.
Figure 16:
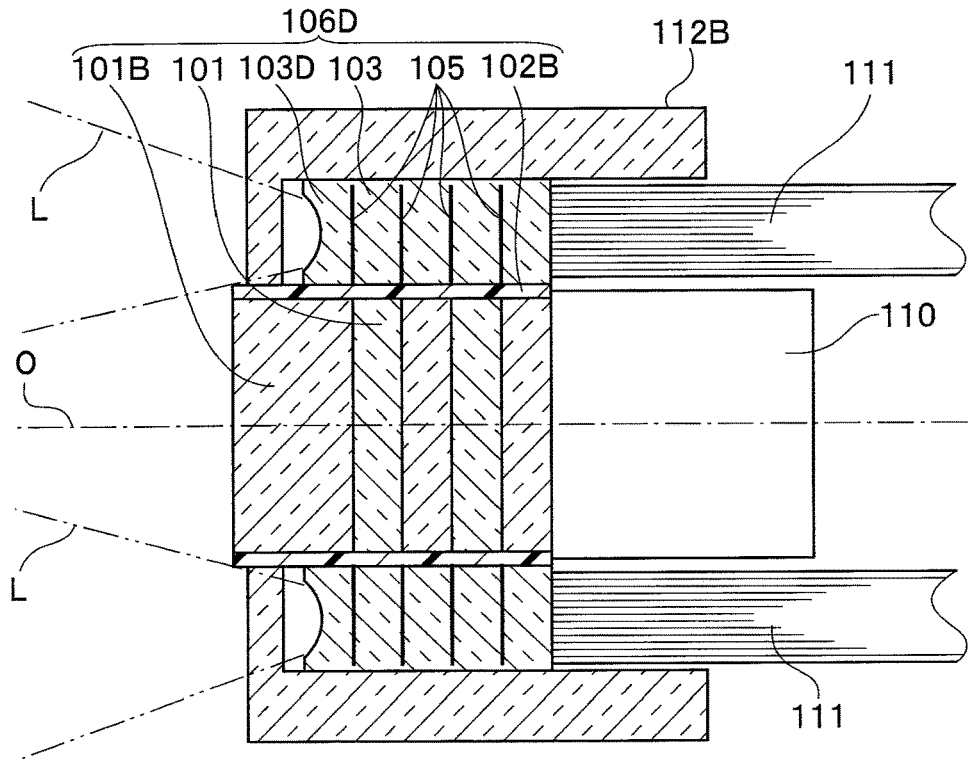
FIG. 16 is an assembly diagram of FIG. 15.

A fifth embodiment of the present invention is a configuration example where a contrivance has been added to the configuration of the illumination optical system of the layered lens array. FIG. 15 and FIG. 16 are diagrams illustrating a configuration example of an endoscope according to the fifth embodiment of the present invention. Among these drawings, FIG. 15 is an exploded view of main parts and FIG. 16 is an assembly diagram.

A basic configuration of the present embodiment is substantially the same as the configuration of the aforementioned third embodiment. The endoscope of the present embodiment is only slightly different in a configuration of an illumination optical system in a layered lens array 106D, which is a layered optical member. The rest of the configuration is substantially the same as the configuration of the aforementioned third embodiment. Therefore, in the following description, only different parts will be described in detail.

The layered lens array 106D applied to the endoscope of the present embodiment has a form in which a plurality of plate members (104D, 104) are coaxially layered in a direction along the optical axis O as illustrated in FIG. 15.

In this case, the second window 103D of the plate member 104D at a distalmost end (second end) of the layered lens array 106D includes a spreading unit (light refraction unit) configured to spread illumination light. In this case, the above spreading unit is formed in a shape concaved from the distalmost end (second end) toward the proximal end (first end) of the layered lens array 106D (optical member).

Note that it is possible to cause illumination light to spread and control light distribution of illumination light by contriving the shape of the spreading unit. The rest of the configuration is substantially the same as the configuration of the aforementioned third embodiment.

As described above, according to the fifth embodiment in such a configuration, it is possible to obtain effects similar to the effects of the aforementioned respective embodiments. Furthermore, according to the present embodiment, the second window 103D of the layered lens array 106D is formed so as to include the spreading unit configured to spread illumination light, and so it is possible to spread illumination light and control light distribution of illumination light.

Note that although an example has been illustrated in the aforementioned fifth embodiment where the second window 103D including the spreading unit is formed on the plate member 104D at the distalmost end of the layered lens array 106D, the present invention is not limited to such a configuration. The second window 103D including the spreading unit may be provided only on one of the second windows included in the layered lens array 106D (optical member). Therefore, the second window 103D including the spreading unit may be provided at any one of the second windows denoted by reference numeral 103 illustrated in FIG. 15 and FIG. 16. With such a configuration, effects similar to the effects according to the aforementioned fifth embodiment can also be obtained. Note that, although the spreading unit is provided at the second window 103D or 103 in the fifth embodiment, it is also possible to provide an optical member (light refraction unit) for causing the fourth window 101B or the first window 101 to refract light, change the view angle of the image pickup optical system or change the focal length.

In the aforementioned respective embodiments, although the first window as the optical lens unit of the image pickup optical system and the second window as the light guide unit of the illumination optical system have been illustrated as having substantially rectangular shapes, the shapes of the first window and the second window are not limited to these examples.

Figure 17:
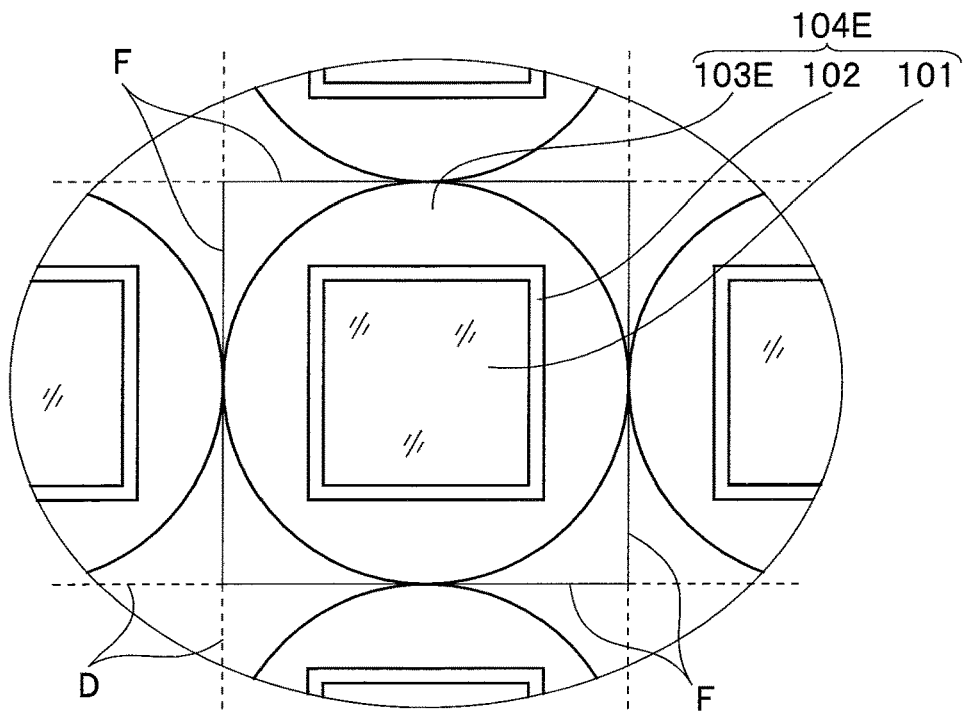
FIG. 17 is a plan view illustrating a first modification of the layered lens array according to each embodiment of the present invention.
Figure 18:
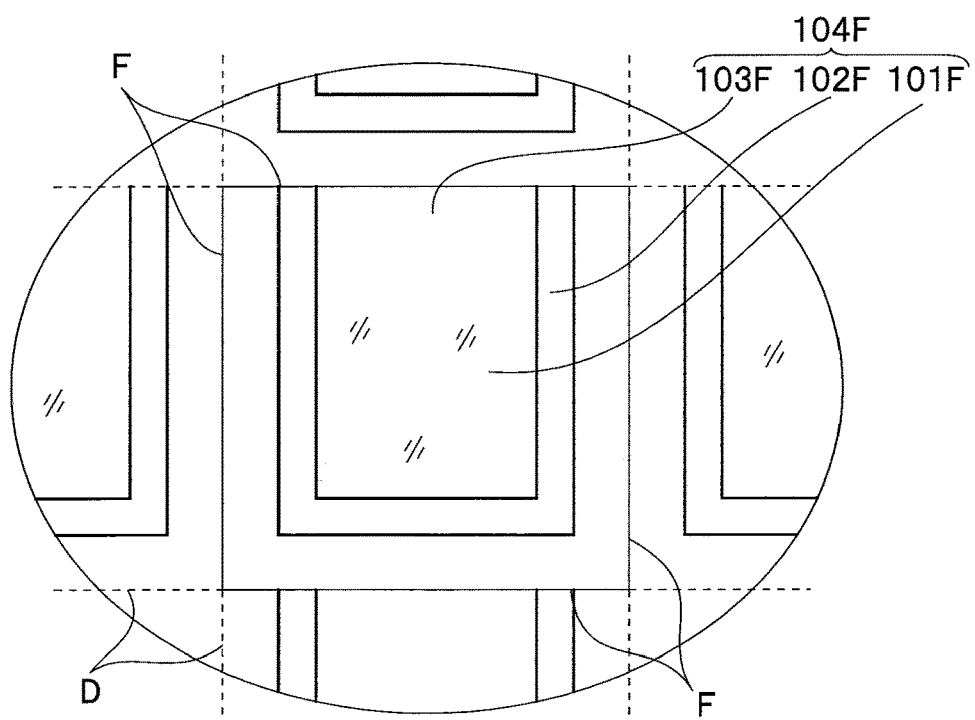
FIG. 18 is a plan view illustrating a second modification of the layered lens array according to each embodiment of the present invention.
Figure 19:
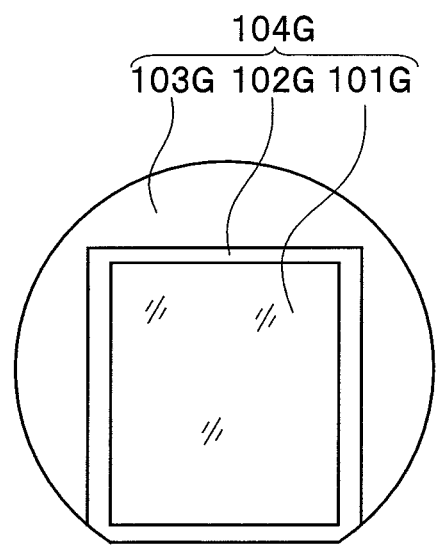
FIG. 19 is a plan view illustrating a third modification of the layered lens array according to each embodiment of the present invention.

FIG. 17 to FIG. 19 are diagrams illustrating various modifications of the layered lens arrays according to the respective embodiments of the present invention.

For example, as illustrated in FIG. 17, the second window 103E of the plate member 104E constituting the layered lens array may be configured to have a circular outer shape.

Depending on the convenience of a molding die, as illustrated in FIG. 18, a configuration may also be considered that a first light-shielding portion 102F is provided on three peripheral sides of a rectangular first window 101F of a plate member 104F constituting the layered lens array and the remaining one side is used as a dicing line. Such a configuration may also be realized with a cover member (not shown) provided so as to surround an outer circumference of a second window 103F.

Furthermore, as illustrated in FIG. 19, a plate member 104G may be configured such that a second window 103G has a substantially circular shape, part of which is notched, one side of a first window 101G is constructed so as to match the notch of the second window 103G and a first light-shielding portion 102G is formed on an outer circumferential edge of the first window 101G.

In this way, even when the respective plate members constituting the layered lens array are configured in various shapes and forms, it is possible to obtain completely the same operations and effects.

The present invention is not limited to the above embodiments, but it goes without saying that various modifications or applications can be made without departing from the spirit and scope of the invention. Furthermore, the above-described embodiments include inventions in various phases and various inventions can be extracted according to appropriate combinations in a plurality of disclosed configuration requirements. For instance, even when some configuration requirements are deleted from all the configuration requirements illustrated in the one embodiment, configurations from which these configuration requirements are deleted can be extracted as inventions as long as the described problems can be solved and the described effects can be achieved. Furthermore, components among different embodiments may be combined as appropriate. The present invention is not restricted by any specific embodiment except being restricted by the appended claims.

Industrial Applicability

The present invention is applicable not only to an endoscope control apparatus in the medical field but also to an endoscope control apparatus in the industrial field.

What is claimed is:

1. A layered wafer lens array comprising:
a plurality of wafer plate members stacked coaxially along an optical axis direction, each wafer plate member comprising:
a first window configured to allow light for forming an optical image to pass through;
a second window configured to allow illumination light to pass through, the second window having an opening defining an inner periphery, and
a light-shielding portion arranged in the opening, the light shielding portion being directly connected to both an outer periphery of the first window and to the inner periphery of the second window; and
an adhesive disposed in a region of the second window between adjacent wafer plate members of the plurality of wafer plate members to fix the adjacent wafer plate members to each other;
wherein the first windows of the plurality of wafer plate members are disposed such that adjacent first windows are stacked in the optical axis direction and the adjacent first windows are aligned in the optical axis direction;
the second windows of the plurality of wafer plate members are disposed such that adjacent second windows are stacked in the optical axis direction and the adjacent second windows are aligned in the optical axis direction; and
the adhesive is disposed between the adjacent second windows stacked in the optical axis direction.

2. The wafer lens array according to claim 1, wherein the adhesive is a transparent adhesive made of a light transmission material.

3. The wafer lens array according to claim 1, wherein the first window of at least one wafer plate member of the plurality of wafer plate members comprises an optical lens.

4. The wafer lens array according to claim 1, wherein the light-shielding portion is connected to both the outer periphery of the first window and to the inner periphery of the second window around an entirety of the outer periphery of the first window and around an entirety of the inner periphery of the second window.

5. A layered wafer lens array comprising:
a plurality of wafer plate members stacked coaxially along an optical axis direction, each wafer plate member comprising:
a first window on which an optical lens configured to allow light for forming an optical image to pass through is disposed;
a second window configured to allow illumination light to pass through, the second window having an opening defining an inner periphery, and
a light-shielding portion arranged in the opening, the light shielding portion being directly connected to both an outer periphery of the first window and to the inner periphery of the second window; and
an adhesive disposed in a region of the second window between adjacent wafer plate members of the plurality of wafer plate members to fix the adjacent wafer plate members to each other;
wherein the first windows of the plurality of wafer plate members are disposed such that adjacent first windows are stacked in the optical axis direction and the adjacent first windows are aligned in the optical axis direction;
the second windows of the plurality of wafer plate members are disposed such that adjacent second windows are stacked in the optical axis direction and the adjacent second windows are aligned in the optical axis direction; and
the adhesive is disposed between the adjacent second windows stacked in the optical axis direction.

6. The layered wafer lens array according to claim 5, wherein the light-shielding portion is connected to both the outer periphery of the first window and to the inner periphery of the second window around an entirety of the outer periphery of the first window and around an entirety of the inner periphery of the second window.

7. A layered wafer lens array comprising:
a plurality of plate members, each comprising:
a first window on which an optical lens configured to allow light for forming an optical image to pass through is disposed;
a second window configured to allow illumination light to pass through, the second window having an opening defining an inner periphery, and
a light-shielding portion arranged in the opening, the light shielding portion being directly connected to both an outer periphery of the first window and to the inner periphery of the second window;
wherein the plurality of plate members are stacked coaxially along an optical axis direction and the stacked plate members are bonded and fixed to each other with an adhesive in a region of the second window such that:
the first windows of the plurality of plate members are disposed such that adjacent first windows are stacked in the optical axis direction and the adjacent first windows are aligned in the optical axis direction;
the second windows of the plurality of plate members are disposed such that adjacent second windows are stacked in the optical axis direction and the adjacent second windows are aligned in the optical axis direction; and
the adhesive is disposed between the adjacent second windows stacked in the optical axis direction.

8. The layered wafer lens array according to claim 7, wherein the light-shielding portion is connected to both the outer periphery of the first window and to the inner periphery of the second window around an entirety of the outer periphery of the first window and around an entirety of the inner periphery of the second window.

9. An image pickup unit comprising:
a layered wafer lens array comprising:
a plurality of wafer plate members stacked coaxially along an optical axis direction, each wafer plate member comprising:
a first window on which an optical lens configured to allow light for forming an optical image to pass through is disposed,
a second window configured to allow illumination light to pass through, the second window having an opening defining an inner periphery, and
a light-shielding portion arranged in the opening, the light shielding portion being directly connected to both an outer periphery of the first window and to the inner periphery of the second window;
an adhesive disposed in a region of the second window between adjacent wafer plate members of the plurality of wafer plate members to fix the adjacent wafer plate members to each other, and an image pickup device disposed so as to face the first window of the layered wafer lens array and on which the optical image is formed;

wherein the first windows of the plurality of wafer plate members are disposed such that adjacent first windows are stacked in the optical axis direction and the adjacent first windows are aligned in the optical axis direction;

the second windows of the plurality of wafer plate members are disposed such that adjacent second windows are stacked in the optical axis direction and the adjacent second windows are aligned in the optical axis direction; and the adhesive is disposed between the adjacent second windows stacked in the optical axis direction.

10. The image pickup unit according to claim 9, wherein the light-shielding portion is connected to both the outer periphery of the first window and to the inner periphery of the second window around an entirety of the outer periphery of the first window and around an entirety of the inner periphery of the second window.

11. An endoscope comprising:

an optical member in which a plurality of wafer plate members are stacked coaxially along an optical axis direction, each wafer plate member of the plurality of wafer plate members comprising:
- a first window configured to allow light for forming an optical image to pass through;
- a second window configured to allow illumination light to pass through, the second window having an opening defining an inner periphery, and
- a light-shielding portion arranged in the opening, the light shielding portion being directly connected to both an outer periphery of the first window and to the inner periphery of the second window;

an adhesive disposed in a region of the second window between adjacent wafer plate members of the plurality of wafer plate members to fix the adjacent wafer plate members to each other;

an image pickup device disposed so as to face the first window at a first end of the optical member and on which the optical image is formed; and an illumination member disposed outside in an outer circumferential direction of the image pickup device so as to face the second window at the first end and configured to emit the illumination light;

wherein the first windows of the plurality of wafer plate members are disposed such that adjacent first windows are stacked in the optical axis direction and the adjacent first windows are aligned in the optical axis direction;

the second windows of the plurality of wafer plate members are disposed such that adjacent second windows are stacked in the optical axis direction and the adjacent second windows are aligned in the optical axis direction; and the adhesive is disposed between the adjacent second windows stacked in the optical axis direction.

12. The endoscope according to claim 11, wherein the light-shielding portion is connected to both the outer periphery of the first window and to the inner periphery of the second window around an entirety of the outer periphery of the first window and around an entirety of the inner periphery of the second window.

13. The endoscope according to claim 11, further comprising:

a transparent cover member comprising: a cover opening corresponding to the first window on a second end of the optical member, the second end being an opposite side of the first end, the transparent cover member being disposed so as to surround a surface facing the second window on the second end and an outer circumferential surface of the optical member.

14. The endoscope according to claim 13, wherein the second window at the second end of the optical member is disposed in the cover opening and made of a member having higher rigidity than the first window.

15. The endoscope according to claim 11, wherein the second end of the optical member further comprising a third window made of a member having higher chemical resistance than the first window and corresponding to the first window, a fourth window made of a member having higher chemical resistance than the second window and corresponding to the second window, and an other light-shielding portion arranged between an outer periphery of the third window and an inner periphery of the fourth window.

16. The endoscope according to claim 11, wherein any second window of the plurality of wafer plate members comprises a light refraction unit configured to spread or converge the illumination light.

17. The endoscope according to claim 16, wherein the light refraction unit has a concave shape from the second end to the first end of the optical member.

* * * * *